(12) United States Patent  (10) Patent No.: US 8,212,102 B2
Kumasaka  (45) Date of Patent: Jul. 3, 2012

(54) DISPOSABLE DIAPER

(75) Inventor: Yoshinori Kumasaka, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 131 days.

(21) Appl. No.: 12/381,732

(22) Filed: Mar. 16, 2009

(65) Prior Publication Data

US 2009/0182298 A1 Jul. 16, 2009

Related U.S. Application Data

(63) Continuation of application No. 09/595,256, filed on Jun. 15, 2000, now abandoned.

(30) Foreign Application Priority Data

Jun. 15, 1999 (JP) .................................. 11-168184

(51) Int. Cl.
*A61F 13/15* (2006.01)
*A61F 13/20* (2006.01)

(52) U.S. Cl. ............... 604/373; 604/385.01; 604/385.24; 604/385.25; 604/385.26; 604/385.27; 604/385.28; 604/385.29; 604/385.3; 604/392; 604/393; 604/394; 604/396; 604/400; 604/401; 604/402; 450/123; 450/132; 2/221; 2/401

(58) Field of Classification Search .................. 604/373, 604/385.01, 385.24–385.3, 392–394, 396, 604/400–402; 450/123, 132; 2/221, 401

See application file for complete search history.

(56) References Cited

U.S. PATENT DOCUMENTS

| | | | |
|---|---|---|---|
| 642,732 A * | 2/1900 | Thom | 2/221 |
| 2,792,698 A | 5/1957 | Hampp | |
| 3,078,469 A * | 2/1963 | Lynam | 2/338 |
| 3,225,764 A | 12/1965 | Magid | |
| 3,414,907 A * | 12/1968 | Flame | 2/221 |
| 3,732,576 A | 5/1973 | Guthier | |
| 4,397,646 A | 8/1983 | Daniels et al. | |
| 4,641,381 A | 2/1987 | Heran et al. | |
| 4,642,818 A | 2/1987 | Dehnert et al. | |
| 4,663,220 A | 5/1987 | Wisneski et al. | |
| 4,735,622 A | 4/1988 | Acuff et al. | |
| 4,861,652 A | 8/1989 | Lippert et al. | |
| 4,883,549 A | 11/1989 | Frost et al. | |
| 4,940,464 A | 7/1990 | Van Gomple et al. | |
| 5,151,092 A * | 9/1992 | Buell et al. | 604/385.3 |

(Continued)

FOREIGN PATENT DOCUMENTS

EP 0688550 12/1995

(Continued)

OTHER PUBLICATIONS

U.S. Appl. No. 09/595,236 BPAI decision of Jan. 16, 2010.*

*Primary Examiner* — Tatyana Zalukaeva
*Assistant Examiner* — Ginger T Chapman
(74) *Attorney, Agent, or Firm* — Brinks Hofer Gilson & Lione

(57) ABSTRACT

A diaper having front and rear waist regions and a waist-hole, the waist hole having a peripheral edge that is elastically stretchable in a circumferential direction and includes covering zones and elastic zones in the front and rear waist regions, which peripheral edge is adapted to be stretchable beyond lengths of the covering zones in the circumferential direction.

7 Claims, 2 Drawing Sheets

U.S. PATENT DOCUMENTS

| | | | |
|---|---|---|---|
| H1440 H * | 5/1995 | New et al. .................. 604/386 |
| 5,500,063 A | 3/1996 | Jessup |
| 5,601,547 A | 2/1997 | Kato et al. |
| 5,607,416 A | 3/1997 | Yamamoto et al. |
| 5,706,524 A * | 1/1998 | Herrin et al. .................. 2/400 |
| 5,711,832 A | 1/1998 | Glaug et al. |
| 5,807,368 A * | 9/1998 | Helmer .................. 604/373 |
| 5,858,013 A | 1/1999 | Kling |
| 5,904,673 A * | 5/1999 | Roe et al. .................. 604/385.3 |
| 6,004,306 A * | 12/1999 | Robles et al. .................. 604/385.21 |
| 6,306,122 B1 | 10/2001 | Naeawa et al. |
| 6,336,921 B1 | 1/2002 | Kato et al. |
| 6,358,350 B1 * | 3/2002 | Glaug et al. .................. 156/204 |
| 6,375,646 B1 | 4/2002 | Widlund et al. |
| 6,547,774 B2 | 4/2003 | Ono et al. |
| 6,551,430 B1 * | 4/2003 | Glaug et al. .................. 156/204 |
| 6,605,173 B2 * | 8/2003 | Glaug et al. .................. 156/204 |
| 2002/0082578 A1 | 6/2002 | Otsubo et al. |

FOREIGN PATENT DOCUMENTS

| | | |
|---|---|---|
| EP | 0941727 | 9/1999 |
| GB | 2294865 | 5/1996 |
| JP | 8038548 A | 2/1996 |
| JP | 10052455 A | 2/1998 |
| JP | 11302902 | 11/1999 |
| WO | WO 96/32083 | 10/1996 |
| WO | WO 97/48357 | 12/1997 |

* cited by examiner

DISPOSABLE DIAPER

RELATED APPLICATION

The present application is a continuation application is U.S. patent application Ser. No. 09/595,256, filed Jun. 15, 2000 now abandoned to which priority is claimed under 35 U.S.C. §120 and through which priority is claimed under 35 U.S.C. §119 to Japanese Patent Application No. 11-168184, filed Jun. 15, 1999.

BACKGROUND OF THE INVENTION

This invention relates to a disposable diaper absorbing and containing body wastes.

Disposable diapers utilizing an inelastic or non-stretchable sheet as their topsheet and/or backsheet are well known. It is also well known in such diapers to secure elastic members under tension in circumferential directions along leg-holes and a waist-hole, respectively, to the inner surface of the topsheet and/or the backsheet and thereby to ensure a good fit of the leg-holes and the waist-hole of the wearer's skin.

In the case of such a well known diaper, a waist size of the diaper has sometimes been dimensioned to be substantially larger than an average waist size of the wearer particularly when the diaper is of the pull-on type so that the diaper may be easily put on the wearer's body with the waist-hole being adequately opened. This is true for the leg-holes. However, such dimensioning has necessarily required an amount of cloth that is much more than a sufficient amount of cloth needed to cover the wearer's legs and waist.

SUMMARY OF THE INVENTION

It is an object of this invention to provide a disposable diaper that is designed to be easily put on the a wearer's body without excessive consumption of cloth.

According to this invention, there is provided a disposable diaper having front and rear waist regions and a crotch region extending therebetween, the diaper comprising at least one of the front and rear waist regions having an edge zone extending in a circumferential direction around a waist-hole being elastic over a full length of the edge, wherein:

the waist region comprises a covering zone formed integrally with the crotch region to position a waist region of the wearer and an elastic zone attached along an upper edge of the covering zone and adapted to be elastically stretchable in the circumferential direction and the elastic zone comprises a first member adapted to be elastically stretchable in the circumferential direction to a length beyond a length of the covering zone and a second member covering the first member, the second member being adapted to be inelastically stretchable to a length beyond the length of the covering zone and to be attached to the upper edge of the covering zone.

The disposable diaper according to this invention enables the elastic zones associated with the waist-hole to be stretched to a length substantially larger than a total length of the edges of the covering zones and thereby to open the waist-hole sufficiently to ensure that the diaper can be easily put on a wearer's body, even when the covering zones of the front and rear waist regions have no stretchability in the circumferential direction. With the diaper, it is unnecessary to dimension a circumferential dimension of the covering zones to be substantially larger than a circumferential dimension of the wearer's torso and therefore stock material required to make the diaper can be correspondingly reduced. Particularly when the rubber ribbon constituting the elastic zone is covered with a non-stretchable sheet previously formed with gathers, it is unnecessary to cover the rubber ribbon with a relatively expensive stretchable sheet.

DETAILED DESCRIPTION OF THE PREFERRED EMBODIMENTS

A disposable diaper according to this invention will be described in more details with reference to the accompanying drawings.

Figure 1:
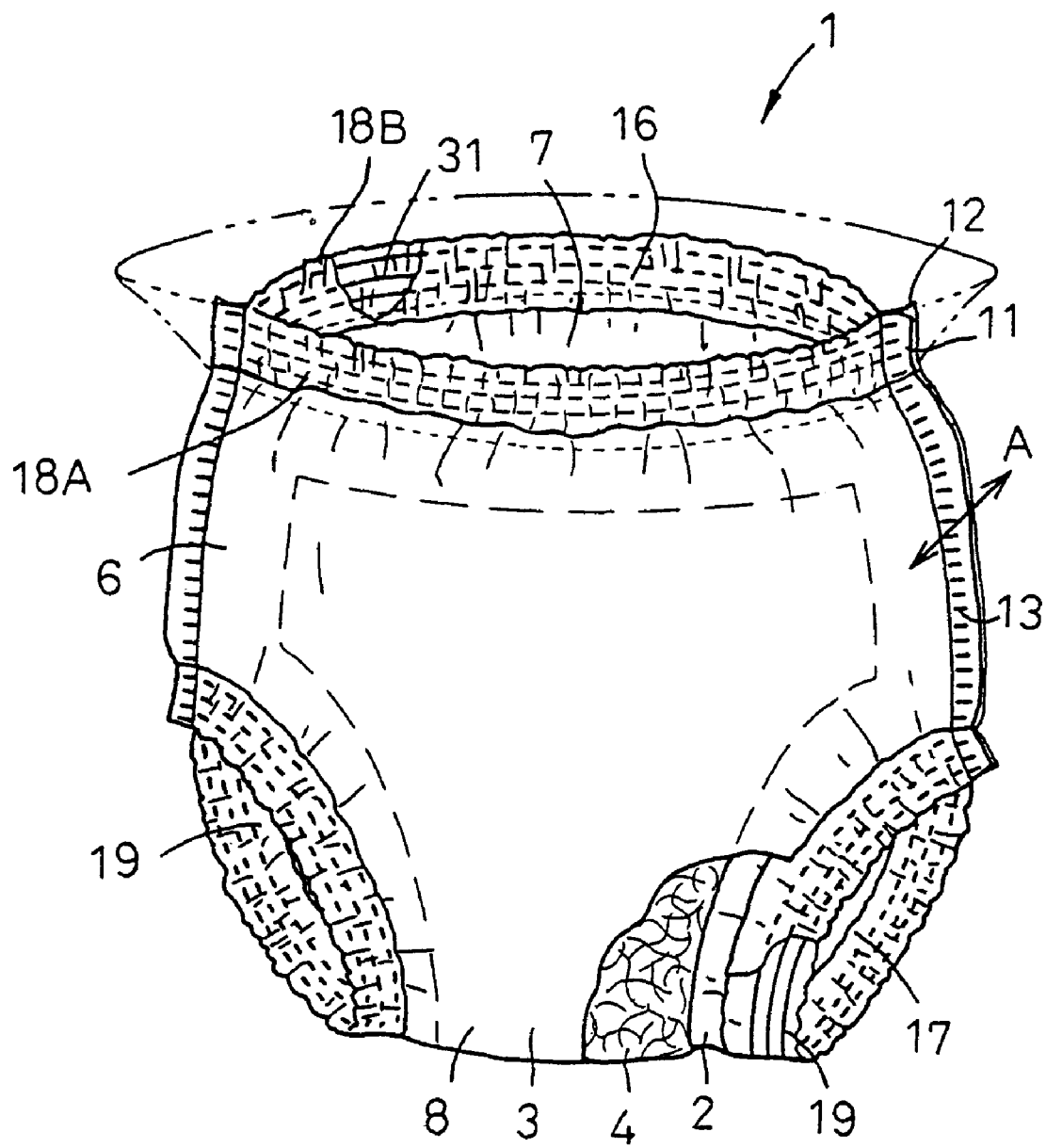
FIG. 1 is a partially cutaway perspective view showing a diaper according to a principle of this invention.

The disposable diaper 1 shown in FIG. 1 in a partially cutaway perspective view is of the pull-on or shorts-type and has a front waist region 6, a rear waist region 7 and a crotch region 8 extending between these two waist regions 6, 7. The front and rear waist regions 6, 7 are put flat together along their respective pairs of transversely opposite side edges 11, 12 and joined together at joining spots 13 arranged along the side edges 11, 12 intermittently in a vertical direction as viewed in FIG. 1 so as to form a waist-hole 16 and a pair of leg-holes 17. An elastic member 18 extends circumferentially around the waist-hole 16 and elastic members 19 extend circumferentially around respective the leg-holes 17. The diaper 1 comprises a liquid-pervious topsheet 2 defining the inner side of the diaper 1, a liquid-impervious backsheet 3 defining the outer side of the diaper 1 and a liquid-absorbent core 4 disposed between the topsheet 2 and the backsheet 3.

Figure 2:
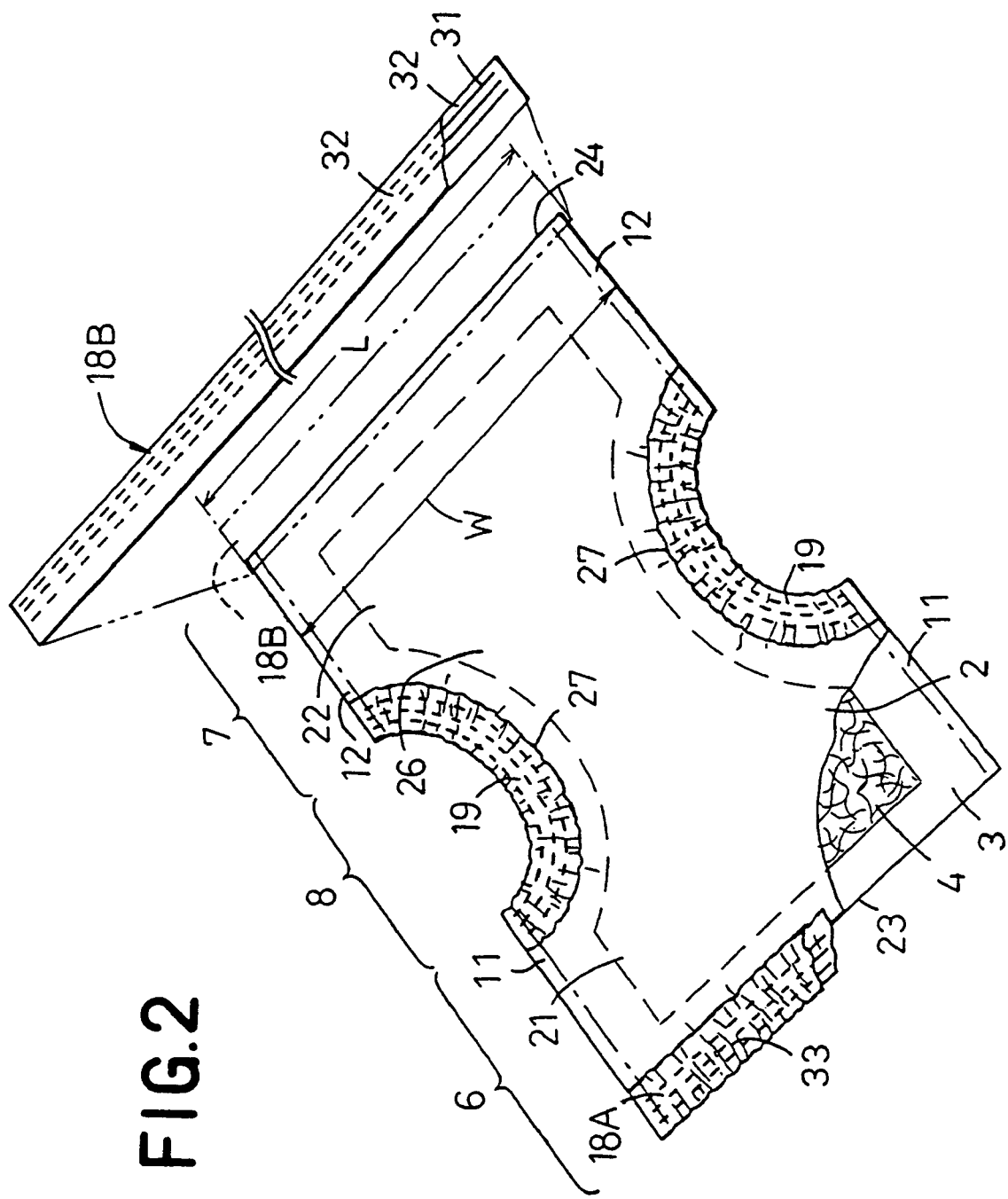
FIG. 2 is a partially cutaway perspective view showing the diaper developed longitudinally thereof.

FIG. 2 is a partially cutaway perspective view of the diaper of FIG. 1 cut open along the joining spots 13 and having its front and rear waist regions 6, 7 developed apart in a direction of double-headed arrow A in FIG. 1. The front and rear waist regions 6, 7 respectively comprise front and rear covering zones 21, 22 adapted to cover front and rear waist regions of the wearer and front and rear elastic ones 18A, 18B identical in shape as well as in size provided along front and rear ends 23, 24 of the respective covering zones 21, 22 extending circumferentially along the waist-hole 16. The crotch region 8 comprises a crotch covering zone 26 adapted to cover a crotch region of the wearer and a pair of elastic zones 19 provided along curved edges 27 of the covering zone 26. The front and rear covering zones 21, 22 and the crotch covering zone 26 are formed by the topsheet 2, the backsheet 3 and the core 4 which are continuous longitudinally of the diaper 1. The core 4 is hourglass-shaped and portions of the topsheet 2 and the backsheets 3 extending outward beyond a peripheral edge of the core 4 are put flat and joined together by means of hot melt adhesive agent (not shown).

The diaper 1 is assembled by putting the traversely opposite side edges 11, 12 of the front and rear waist regions 6, 7 flat together, then joining them together at the joining spots 13 and thereby an annular elastic zone 18 is formed by the front and rear elastic zones 18A, 18B. Of the front and rear elastic zones 18A, 18B, the rear elastic zone 18B is illustrated in a state before elastic zone 18B is attached to the rear covering zone 22. The rear elastic zone 18B comprises a rubber ribbon 31 which can be elastically stretched by at least 1.3 times, preferably by 2.0 times, more preferably by at least 3.0 times of a length L of the rear waist region 7 and a covering sheet 32 adapted to cover the rubber ribbon 31, which covering sheet 32 is longer than the dimension L and stretchable at least at the stretchability of the rubber ribbon 31. The number of the rubber ribbons 31 and their shape as well as the dimension of their cross-section are not specified. Raw material for the rubber ribbon 31 also is not specified and may be selected from a group including natural rubber, synthetic rubber, synthetic resin elastomer, synthetic resin elastic threads and a woven fabric made of such elastic threads, However, it is important that the front and rear elastic zones 18A, 18B each comprising an assembly of the rubber ribbon 31 and the covering sheet 32 should have their circumferential stretch stress preferably when they are stretched by 3~20% lower than a stretch stress exhibited by portions of the front and rear covering zones 21, 22 extending along the elastic zones 18A, 18B having the same widths as the elastic zones 18A, 18B. Generally, the covering sheet 32 is longer than the dimension L and inelastically or elastically stretched as the rubber ribbon 31 is elastically stretched. For example, a non-stretchable sheet longer than the dimension L is formed with gathers 33 undulating in the circumferential direction along the waist-hole to make this sheet substantially stretchable and this covering sheet 32 is attached to the rear covering zone 22. Alternatively, the covering sheet 32 can comprise an inelastically stretchable sheet attached to the rear covering zone 22 so that the sheet may be stretched as the rubber ribbon 31 is stretched and form gathers as the rubber ribbon 31 contracts. It is also possible to use a covering sheet 32 adapted to be elastically stretched together with the rubber ribbon 31.

The rubber ribbon 31 may be covered with a pair of covering sheets 32 in a sandwich fashion or covered with a covering sheet 32 that is cylindrically shaped adapted to receive the rubber ribbon 31 therein. In any case, the rubber ribbon 31 is secured to the covering sheet(s) 32 at least at longitudinally opposite ends of the rubber ribbon 31 or, if desired, a length of the rubber ribbon 31 defined between the opposite ends is intermittently or continuously bonded to the covering sheet(s) 32. In a specific embodiment shown in FIG. 2, three to five pieces of synthetic rubber ribbon 31 each having a thickness of 0.3 mm, a width of 2.1 mm and a length of 171 mm are stretched to 400 mm and intermittently bonded to a pair of non-stretchable covering sheets 32 made of a spunbond nonwoven fabric and having a length of 400 mm by means of a hot melt adhesive agent (not shown) so as to cover the rubber ribbons 31 with the covering sheets 32 in sandwich fashion and thereby to obtain the rear elastic zone 18B. The rubber ribbons 31 are relaxed so as to contract and thereby cause the sheets 32 to form gathers 33. The rear elastic zone 18B contracted to a length of 240 mm in this manner is attached to the rear covering zone 22 having the length L of 240 mm as measured along the waist line by suitable means such as adhesion, heat-sealing or stitching.

With the diaper 1, the elastic zone 18 associated with the waist-hole 16 is stretched as indicated by the imaginary lines in FIG. 1 and said waist-hole 16 is adequately opened so that the diaper 1 can be easily put on the wearer's body even when the front and rear covering zones 21, 22 have no stretchability in the circumferential direction.

With this diaper 1, in a manner similar to the elastic zone 18 associated with the waist-hole 16, each of the elastic zones 19 associated with the leg-holes 17 should be elastically stretchable to a dimension longer than, at least by 1.3 times, preferably at least by 2 times and more preferably at least by 3 times of an actual dimension as measured along the length surrounding edge 27 of the crotch covering zone 26. Such elastic zone 19 may comprise elastically stretchable rubber ribbon and a stretchable covering sheet.

As will be apparent from the foregoing description made with reference to the accompanying drawings, either both the longitudinal ends of the front and rear waist regions 6, 7 or any one of these ends may be provided with an elastic stretchability in accordance with this invention. It is possible without departing from the scope of this invention to adjust the stretch stresses of the elastic zones 18A, 18B associated with the front and rear waist regions 6, 7 to be different from each other. Well known stock materials may be used to form the topsheet 2 and the backsheet 3 and the core 4. Bonding of the respective members may be performed using suitable means such as adhesions, heat-sealing or stitching.

What is claimed is:
1. A disposable diaper comprising:
a topsheet;
a backsheet;
a front waist region extending between and to transversely opposite side edges of the disposable diaper;
a rear waist region extending between and to the transversely opposite side edges of the diaper;
a crotch region located longitudinally between the front waist region and the rear waist region;
a waist-hole; and
a pair of leg-holes, said diaper further comprising:
at least one of said front and rear waist regions including a covering zone formed integrally with said crotch region, said covering zone including a longitudinal end at which longitudinal ends of each of said topsheet and backsheet are superimposed together continuously between the transversely opposite side edges of the diaper without any intervening structure between the topsheet and backsheet, said covering zone further including a terminal longitudinal edge which coincides with and is coextensive with terminal longitudinal edges of each of said top sheet and backsheet, said at least one of said front and rear waist regions further including an elastic zone, said elastic zone:
extending continuously along a full length in a circumferentially direction of said at least one of said front and rear waist regions to define at least part of said waist-hole;
having a width defined in a longitudinal direction and attached directly to said topsheet so that a major portion of the width of said elastic zone extends beyond the terminal longitudinal edge of said covering zone and the terminal longitudinal edges of each of said top sheet and backsheet;
being nonmonolithically formed with the covering zone;
including a first member that is elastically stretchable in said circumferential direction of said at least one of said front and rear waist regions to a length greater than a transverse length of said covering zone, said first member extending between and to the transversely opposite side edges of the diaper; and
including a second member covering said first member, said second member also extending between and to the transversely opposite side edges of the diaper, said second member being inelastically stretchable and having a length greater than the transverse length of said covering zone and attached to the terminal longitudinal edge of said covering zone so as to form gathers that extend along the entire length of said at least one of said front and rear waist regions in the circumferential direction between and to each of the opposite side edges of the diaper,
said elastic zone being formed by:
attaching the second member to the first member so that when the first member contracts gathers are formed in the second member so that overall gathered length of said second member is substantially equal to the length of the covering zone; and attaching the gathered second member to the covering zone.

2. The diaper according to claim 1, wherein said first member comprises at least one a rubber ribbon.

3. The diaper according to claim 1, wherein said covering zone is non-stretchable in said circumferential direction of said at least one of said front and rear waist regions.

4. The diaper according to claim 1, wherein said covering zone is elastically stretchable in said circumferential direction and has a stretch stress higher than a stretch stress of said elastic zone when said elastic zone is stretched by 3-20% in a portion of said covering zone extending along said elastic zone and having a same width as said elastic zone.

5. The diaper according to claim 1, wherein each of said leg-holes comprises a covering zone integral with said crotch region and a continuous elastic zone extending along a full length in a circumferential direction of each of said leg-holes, said elastic zone including a third member that is elastically stretchable in said circumferential direction of each of said leg holes and a fourth member securing and covering said third member, said fourth member being inelastically stretchable to a length greater than said full length in said circumferential direction of each of said leg-holes and joined to an outer side edge of each of said leg-holes.

6. The diaper according to claim 1, wherein the second member comprises a pair of cover members between which the first member is sandwiched.

7. The diaper according to claim 1, wherein said elastic zone has a circumferential stretch stress when stretched by 3-20% that is lower than a stretch stress of portions of the front and rear covering zones extending along the elastic zones.

* * * * *